United States Patent [19]

Alam et al.

[11] Patent Number: 4,879,286

[45] Date of Patent: Nov. 7, 1989

[54] CYCLOPHOSPHAMIDE

[75] Inventors: Abu S. Alam, Libertyville; Kenneth J. Koziol, Bensenville; John N. Kapoor, Lake Forest, all of Ill.

[73] Assignee: Lyphomed, Inc., Rosemont, Ill.

[21] Appl. No.: 178,761

[22] Filed: Apr. 4, 1988

Related U.S. Application Data

[63] Continuation of Ser. No. 8,598, Jan. 28, 1987, abandoned.

[51] Int. Cl.$^4$ .............................................. A61K 31/66
[52] U.S. Cl. ..................................................... 514/110
[58] Field of Search ......................................... 514/110

[56] References Cited

U.S. PATENT DOCUMENTS

| | | | |
|---|---|---|---|
| 3,018,302 | 1/1962 | Arnold et al. | 260/461 |
| 3,732,340 | 5/1973 | Arnold et al. | 260/936 |
| 4,537,883 | 9/1987 | Arnold et al. | 514/960 |

FOREIGN PATENT DOCUMENTS 2084154  4/1982  United Kingdom ................ 514/110

*Primary Examiner*—Jerome D. Goldberg
*Attorney, Agent, or Firm*—Leydig, Voit & Mayer, Ltd.

[57] ABSTRACT

A storage-stable liquid oncolytic formulation of cyclophosphamide for parenteral administration is presented. Currently utilized lyophilized formulations have inherent diseconomies and increased hazard is associated with reconstitution. The liquid formulations of the present invention comprise a solution of cyclophosphamide with an organic polyol as cosolvent, which provide enhanced shelf-life and greater ease of administration. The polyol is either propylene glycol, polyethylene glycol or glyerol. The solution of cyclophosphamide is either aqueous, or in the case of propylene glycol may constitute 10-30% by weight of an alcohol.

1 Claim, No Drawings

CYCLOPHOSPHAMIDE

BACKGROUND OF THE INVENTION

Cyclophosphamide is the generic name for 2-[bis(2-chloroethyl)amino]tetrahydro-2H-1,3,2-oxazaphosphorine-2-oxide monohydrate, a widely used antineoplastic drug chemically related to the nitrogen mustards. The nitrogen mustards are known as alkylating agents. These alkylating agents undergo strongly electrophilic reactions with such biologically important molecules as DNA. By alkylating DNA, these agents interfere with replication which ultimately interferes with cell viability. When exposed to these alkylating agents at low doses, the cell is capable of remaining viable by relying on its DNA repair enzymes which remove these alkylators prior to replication, thus allowing replication to proceed normally. The efficiency of these repair enzymes will be related to the degree and type of alkylation which must be repaired. For example, alkylation of a single strand of DNA may often be repaired with relative ease allowing normal cell division. However, damage to DNA caused by interstrand cross linkers (bifunctional agents such as cyclophosphamide) are more difficult to repair and involve more complex mechanisms. Thus, with increasing doses there is more extensive cross linking resulting in DNA breakdown with concomitant cell death.

These agents are cell cycle nonspecific being capable of combining with cells at any phase of their cycle. The therapeutic efficacy of these compounds arises from their interference with replication in cells which are dividing faster than their DNA repair enzymes can de-alkylate. It is through this destructive interference with replication in these rapidly dividing cells which these alkylating agents exert their cytotoxicity.

Cancer cells are notorious for being just such rapidly proliferating cells. This affords the pharmacologist a target at which chemotherapeutic agents may be aimed. Cancerous tissue growth outpaces the corrective effect of the DNA repair enzymes. These tissues then undergo extensive cell death due to breakdowns in replication and tissue growth falls off.

Cyclophosphamide was one example of a group of novel cyclic phosphoric acid ester amides which were disclosed and claimed in U.S. Pat. No. 3,018,302 granted Jan. 23, 1962 to H. Arnold et al.

A related series of compounds bearing substituents on the oxazaphosphorine ring nitrogen was disclosed and claimed in U.S. Pat. No. 3,732,340 granted May 8, 1973 also to H. Arnold et al.

Early in its clinical application cyclophosphamide was available as the monohydrate in parenteral dosage formulations consisting of sterile packaged dry powder blend admixtures of the drug and sodium chloride. The premixes were dissolved in water prior to administration which could be oral as well as parenteral. The aqueous solution, however, necessitated prompt administration in that shelf-life was limited to several hours after preparation. Moreover, during processing and/or storage of the dry powder premix formulation, a glassiness and/or stickiness could be acquired by the premix composition giving an unattractive material with inferior solubility characteristics and decreased potency. This deterioration was more pronounced as storage time was extended or if the upper limit of the storage temperature range was exceeded.

This temperature susceptibility was problematic in that a common practice in the constitution of sterile solids involves heating the mixture to expedite the dissolution process. It has been shown, however, that warming vials of cyclophosphamide in order to facilitate dissolution, after adding an aqueous vehicle, could decrease the potency of the final injectable product. D. Brooke et al., *American Journal of Hospital Pharmacy* 32:44–45 (1975). Subsequently, these stability limitations and dissolution difficulties were recognized as substantial shortcomings which often resulted in clinical use of subpotent cyclophosphamide solutions.

As a result of this thermal and hydrolytic susceptibility, workers in the art turned to lyophilization. The technique known as lyophilization is often employed for injectable pharmaceuticals which exhibit poor stability in aqueous solution. This process involves freeze drying, whereby ice is sublimed from frozen solutions leaving only the solid, dried components of the original liquid. On Aug. 27, 1985 a patent issued to R. L. Alexander et al. which disclosed and claimed process and preparations for lyophilized cyclophosphamide.

Lyophilization has several advantages over the previous dry powder formulations. Lyophilization permits pharmaceuticals which are unstable in aqueous solution, yet relatively stable in the solid state to be processed and filled into dosage containers in solution, taking advantage of the relative ease of processing a liquid; dried without elevated temperatures, thereby eliminating adverse thermal effects; and then stored in the dry state in which there are relatively few stability problems.

Lyophilization has several accompanying disadvantages as well. The lyophilization process is costly, inefficient and dangerous.

Lyophilization requires sophisticated vacuum pumps, sterile, refrigerated chambers with meticulous thermal controls for cooling samples, condensors to trap the water vapor as it sublimes from the frozen solution, and thermocouple probes for monitoring product temperature. The apparatus itself, the energy and the technicians required to run it become quite expensive on an industrial scale and raise the cost of the product accordingly.

Lyophilization is inefficient. Lyophilization involves removing water from a frozen aqueous solution leaving a freeze-dried solid, shipping the freeze-dried solid to the customer, who, when necessary, reconstitutes the drug as an aqueous solution. Clearly, if the lyophilization process could be circumvented, time and cost would be reduced.

The lypholized product must be reconstituted. Reconstitution necessitates some degree of personnel exposure. This is particularly undesirable when the drug is a strongly cytotoxic antineoplastic agent. This hazardous personnel exposure is aggravated by aerosolization of the potent cytotoxic agent. As a lyophilizate the drug must be dissolved prior to removal for injection. This necessitates additional entry to the vial with a syringe to add the solubilizing liquid vehicle. With each accession of the vial small quantities of the drug become airborne and this is known as aerosolization. Such added exposure requires particular precautions such as rubber gloves and masks. Furthermore, reconstitution introduces potential for dilution errors. For these and other reasons producers and consumers alike prefer readily injectable liquid formulations of parenterally administered drugs.

Heretofore, it has been generally recognized that liquid formulations of cyclophosphamide would not be possible due to the inherent instability of cyclophosphamide in water. It was unexpectedly discovered, however, that stable solutions of cyclophosphamide for parenteral or oral administration are, in fact, possible. This occurs when cyclophosphamide is dissolved in a solution containing an organic solvent, such as a polyol, preferably propylene glycol, polyethylene glycol or glycerol, or combinations thereof. (See Tables 1 and 2.)

SUMMARY OF THE INVENTION

The present invention provides stable liquid oncolytic formulations for parenteral administration comprising cyclophosphamide in a carrier which comprises from about 50 to about 100% of an organic polyol and from about 0 to about 50% water.

Thus, this invention provides improved liquid pharmaceutical formulations of cyclophosphamide which have improved stability and shelf-life. These desirable stabilized compositions are solutions comprising propylene glycol, polyethylene glycol, or glycerol, or combinations thereof, and water. Most notably a solution comprising as the carrier about 80% propylene glycol and about 20% polyethylene glycol 400 gives the greatest stability for the dissolved cyclophosphamide.

DETAILED DESCRIPTION OF THE PREFERRED EMBODIMENTS

The therapeutically active component of this invention, cyclophosphamide, is a well known and widely used anticancer agent. Cyclophosphamide chemically is [2-[bis-(2-chloroethyl) amino]tetrahydro-2H-1, 3, 2-oxazaphosphorine-2-oxide]monohydrate. It is appreciated by the practitioner that the degree of reactivity desired for efficacy in an agent of this sort necessarily acts as a limit to its inherent stability in aqueous solution. Mainly for this reason cyclophosphamide has historically been compounded as a sterile dry powder mixture of cyclophosphamide monohydrate and sodium chloride for reconstitution with Water for Injection or as the lyophilized solid with mannitol excipient for reconstitution with Water for Injection. Both procedures require costly, extensive processing in production and time-consuming hazardous handling in preparation or reconstitution. Additionally, both compositions lead to costly waste due to very short shelf-life of the reconstituted solutions. Consequently, portions not used immediately must be discarded.

The instant invention has resulted from work undertaken to ascertain if the stability of cyclophosphamide in solution can be improved thereby allowing the marketing of such formulations and obviating the aforementioned shortcomings of dry powder mixtures and lyophilized compositions.

As indicated previously, the liquid oncolytic formulations of the present invention have as the carrier from about 50 to about 100% of an organic polyol and from about 0 to about 50% water. The organic polyols which are useful in the present invention include propylene glycol, polyethylene glycol, glycerol, and mixtures thereof. The polyethylene glycols typically will have molecular weights from about 190 to about 600.

As is well known in the art, the presence of water in a carrier vehicle for cyclophosphamide provides a ready means for the degradation through hydrolysis of the cyclophosphamide. However, it has been discovered that through the use of the present invention, water may be present in amounts up to about 50% based on the total weight of the liquid carrier, and one may still obtain formulations with useful stability, in comparison to a purely aqueous solution.

Most preferably, no water is present in the formulations of the present invention. Also, it is preferable to use as the carrier, mixtures of propylene glycol and polyethylene glycol, particularly mixtures in which the propylene glycol is present from about 10 to about 90%, and the polyethylene glycol is present in amounts from about 90 to about 10%, based on the total weight of the carrier. An especially useful formulation contains from about 70 to about 90% propylene glycol and from about 10 to about 30% polyethylene glycol, particularly about 80% propylene glycol and about 20% polyethylene glycol.

The amount of cyclophosphamide which may be present in the formulations of the present invention can be quite varied. In an aqueous formulation, the cyclophosphamide is restricted to the solubility limit of the cyclophosphamide in water which is about 33 milligrams per ml of solution. By contrast, the present invention can provide formulations containing up to about 1000 milligrams of cyclophosphamide per ml of solution. Typically, from about 5 to about 1000 mg of cyclophosphamide per ml of solution. Preferably, the formulations of the present invention will take advantage of the discovered solubility of the cyclophosphamide in the carrier and will contain from about 5 up to about 1000 milligrams of cyclophosphamide per ml.

By referring to the subsequent examples, it can be seen that several of the formulations of the present invention show surprisingly good stability. Furthermore, the example support the following conclusions: a) the inclusion of water up to about 50% of the liquid vehicle still results in a solution having useful stability characteristics; b) a 100% organic vehicle show unexpectedly increased stability; c) that an 80:20 mixture of propylene glycol and polyethylene glycol imparts the most improved stability; and d) there is no significant difference in stability between 20 mg/ml and 100 mg/ml of cyclophosphamide in the formulations. Furthermore, it is likely that the desired stability of cyclophosphamide will also be achieved with the formulations of the present invention in combination with alcohols such as ethanol. Wherein ethanol is present in an amount 10-30% based on total weight of the formulation.

The formulations of the present invention provide a number of important advantages. The liquid formulations provide a simple method of dosing. No reconstitution is necessary. Cyclophosphamide has greater solubility in the liquid carrier used in the present formulations. Thus, the concentration of cyclophosphamide in the formulations of the present invention can be as high or 1000 mg/ml whereas the highest concentration achievable with water is only 33 mg/ml. Consequently, less volume of solution needs to be injected into the patient for administering the same amount of drug. This is particularly beneficial for intramuscular injections.

Additional advantages of the formulations of the present invention include increased safety by virtue of the decreased amount of manipulation by, and hence exposure to, clinicians, of the active agent; increased assurance of sterility; and decreased likelihood of errors in dosing.

The present invention will be further described by way of the following non-limiting examples.

EXAMPLES 1-11

General Procedure

Previous studies have shown that the degradative process for cyclophosphamide follows first order kinetics. The degradation of cyclophosphamide, either in lyophilized form or aqueous solution results from hydrolysis and the loss of a chloride ion. This chloride ion can be very easily titrated to determine its concentration. In other words, the stability of cyclophosphamide can be easily determined by chloride ion titration.

Additionally, temperature variation can be an effective tool in determining drug stability. For a degradative process which follows first order kinetics, an increase in temperature causes a calculatable increase in the decomposition rate. For this reason, temperature effect studies are routinely carried out during storage testing. Tests known as accelerated storage tests have found wide use in determining the effects of given factors on drug stability under conditions of normal storage but in which the temperature factor is exaggerated.

Eleven formulations were prepared containing the carrier and amount of cyclophosphamide as set forth in Table I. Examples 4 and 8 are controls in which the cyclophosphamide is dissolved in 100% water as the carrier. Examples 1, 2, 5 and 6 are comparative Examples in which greater than 50% water is present in the carrier vehicle. After preparation the formulations are subjected to accelerated storage tests.

In the accelerated storage tests, samples of each formulation (Examples 1-11) were stored in each of four thermal environments (refrigerated, room temperature, 30° C. and 40° C.). The stored samples were generally examined after 1 week, 2 weeks, 9 weeks and 11 weeks and some after 15 weeks. The amount of cyclophosphamide remaining at each juncture was determined by chloride ion titration and the results of the study are set forth in Tables 2-5.

From the data in Tables 2-5, it is found that the liquid formulations of the present invention have superior storage properties when compared with the formulations comprised of 100% water, or the comparative formulations containing over 50% water. The most preferred formulations of the present invention have a minimum shelf-life of 12 months when stored under refrigeration.

TABLE 1

CYCLOPHOSPHAMIDE FORMULATIONS

| Example | 1 | 2 | 3 | 4 | 5 | 6 | 7 | 8 | 9 | 10 | 11 |
|---|---|---|---|---|---|---|---|---|---|---|---|
| Propylene Glycol | 25% | | 25% | | 25% | | 25% | | 50% | 80% | 80% |
| Polyethylene Glycol | | | | | | | | | | 20% | 20% |
| Glycerol | | 25% | 25% | | | 25% | 25% | | 50% | | |
| Water for Injection | 75% | 75% | 50% | 100% | 75% | 75% | 50% | 100% | | | |
| Cyclophosphamide (mg/ml) | 5 | 5 | 5 | 5 | 20 | 20 | 20 | 20 | 20 | 20 | 100 |

TABLE 2

PERCENT CYCLOPHOSPHAMIDE (4° C.)

| Example | Zero Time | 1 Week | 2 Weeks | 9 Weeks | 11 Weeks | 15 Weeks |
|---|---|---|---|---|---|---|
| 1 | 100 | 96.0 | 93.8 | | | |
| 2 | 100 | 96.8 | 93.7 | | | |
| 3 | 100 | 96.8 | 92.5 | | | |
| 4 | 100 | 97.2 | 94.8 | | | |
| 5 | 100 | 99.4 | 96.4 | | 73.1 | |
| 6 | 100 | 97.8 | 94.7 | | 71.0 | |
| 7 | 100 | 99.1 | 96.8 | | 73.4 | |
| 8 | 100 | 97.7 | 95.0 | | 87.0 | 70.8 |
| 9 | 100 | 99.4 | 99.3 | | 96.2 | |
| 10 | 100 | 99.2 | 98.5 | | 98.7 | |
| 11 | 100 | | 99.4 | 97.3 | | |

TABLE 3

PERCENT CYCLOPHOSPHAMIDE (ROOM TEMPERATURE)

| Example | Zero Time | 1 Week | 2 Weeks | 9 Weeks | 11 Weeks |
|---|---|---|---|---|---|
| 1 | 100 | 83.5 | 71.7 | | |
| 2 | 100 | 80.8 | 70.2 | | |
| 3 | 100 | 84.8 | 73.7 | | |
| 4 | 100 | 81.4 | 69.6 | | |
| 5 | 100 | 83.3 | 72.2 | | |
| 6 | 100 | 81.5 | 70.8 | | |
| 7 | 100 | 85.6 | 76.1 | | |
| 8 | 100 | 81.8 | 70.5 | 0.1 | |
| 9 | 100 | 97.6 | 94.1 | 74.4 | |
| 10 | 100 | 98.9 | 97.1 | 86.6 | |
| 11 | 100 | 96.7 | 88.0 | | |

TABLE 4

PERCENT CYCLOPHOSPHAMIDE (30° C.)

| Example | Zero Time | 1 Week | 2 Weeks | 9 Weeks | 11 Weeks |
|---|---|---|---|---|---|
| 1 | 100 | 60.0 | 36.3 | | |
| 2 | 100 | 56.8 | 32.9 | | |
| 3 | 100 | 64.4 | 43.2 | | |
| 4 | 100 | 56.5 | 32.4 | | |
| 5 | 100 | 61.9 | 40.8 | | |
| 6 | 100 | 57.8 | 36.2 | | |
| 7 | 100 | 65.7 | 46.5 | | |
| 8 | 100 | 55.9 | 33.1 | | |
| 9 | 100 | 90.9 | 89.4 | 22.2 | |
| 10 | 100 | 95.2 | 89.4 | 54.1 | |
| 11 | 100 | 91.1 | 58.6 | | |

TABLE 5

PERCENT CYCLOPHOSPHAMIDE (40° C.)

| Example | Zero Time | 1 Week | 2 Weeks |
|---|---|---|---|
| 1 | 100 | 0 | 0 |
| 2 | 100 | 0 | 0 |
| 3 | 100 | 2.7 | 0 |
| 4 | 100 | 0 | 0 |
| 5 | 100 | 0 | 0 |
| 6 | 100 | 0 | 0 |
| 7 | 100 | 5.1 | 0 |
| 8 | 100 | 0 | 0 |
| 9 | 100 | 74.6 | 49.3 |
| 10 | 100 | 86.5 | 71.5 |
| 11 | 100 | | 78.7 |

What is claimed is:

1. A storage-stable, liquid oncolytic formulation for parenteral administration comprising a solution of cyclophosphamide in a substantially anhydrous carrier which comprises about 80 percent propylene glycol and about 20 percent polyethylene glycol, wherein the cyclophosphamide is present in an effective amount up to about one gram per milliliter of solution.

* * * * *